(12) United States Patent
Blay et al.

(10) Patent No.: US 7,354,705 B2
(45) Date of Patent: Apr. 8, 2008

(54) METHODS FOR CANCER PROGNOSIS AND DIAGNOSIS

(75) Inventors: Jean-Yves Guy Christophe Blay, Frontonas (FR); Isabelle Andrée Lucette Treilleux, Lyons (FR); Jean-Jacques Pin, St. Bonnet de Mure (FR); Serge Joseph Emma Lebecque, Civrieux d'Azergues (FR)

(73) Assignee: Schering Corporation, Kenilworth, NJ (US)

( * ) Notice: Subject to any disclaimer, the term of this patent is extended or adjusted under 35 U.S.C. 154(b) by 378 days.

(21) Appl. No.: 10/766,230

(22) Filed: Jan. 27, 2004

(65) Prior Publication Data

US 2004/0229297 A1 Nov. 18, 2004

Related U.S. Application Data

(60) Provisional application No. 60/443,825, filed on Jan. 30, 2003.

(51) Int. Cl.
*G01N 33/48* (2006.01)
*G01N 33/50* (2006.01)

(52) U.S. Cl. ............................................ 435/4; 436/64
(58) Field of Classification Search ..................... None
See application file for complete search history.

(56) References Cited

FOREIGN PATENT DOCUMENTS

WO    WO 03/033667   *  4/2003
WO    WO 03/087347   *  10/2003

OTHER PUBLICATIONS

Lissoni et al (Journal of Biological Regulators and Homeostatic Agents, 1999, vol. 13, pp. 216-219).*
Schnorr et al, Journal of Virology, 1993, vol. 67, pp. 4760-4768.*
Liu, Human Immunology, 2002, vol. 63, pp. 1067-1071.*

* cited by examiner

*Primary Examiner*—Karen A. Canella
(74) *Attorney, Agent, or Firm*—Gloria M. Fuentes

(57) ABSTRACT

The invention provides methods for prognosis and diagnosis in human cancer patients comprising detecting in human tumor tissues the infiltration of certain immune cells associated with poor cancer prognosis. The methods are useful for making clinical decisions on cancer treatment, surveillance and surgical intervention.

5 Claims, No Drawings

METHODS FOR CANCER PROGNOSIS AND DIAGNOSIS

CROSS-REFERENCE TO RELATED APPLICATIONS

This application claims priority to U.S. Provisional Application No. 60/443,825, filed Jan. 30, 2003, which is incorporated herein by reference.

FIELD OF THE INVENTION

The invention provides methods for prognosis and diagnosis in human cancer patients comprising detecting in human tumor tissues the infiltration of certain immune cells associated with poor cancer prognosis. The methods are useful for making clinical decisions on cancer treatment and surveillance.

BACKGROUND OF THE INVENTION

Breast cancer is the most frequent malignant tumor of women in western countries. The prognosis of early breast carcinoma is influenced by several clinical and biological parameters. Among these, signs of early dissemination such as presence of tumor cell in the regional lymph nodes, and possibly in the bone marrow, are well established adverse prognostic factors (Solomayer et al., 2001, Clin Cancer Res 7(12):4102-8; Schnitt S. J., 2001, J. Natl. Cancer Inst Monogr 30:22-6). In addition, the phenotypic and molecular characteristics of the tumor, especially histological grade, hormone receptor expression and HER2 amplification behave as both prognostic factors for relapse and death and predictive factors for responsiveness to hormone and cytotoxic therapy (Fitzgibbons et al., 1999, Arch. Pathol. Lab. Med. 124(7):966-78).

Evidence suggests that the immune response may also influence the progression of tumors. The concept of tumor immunosurveillance, proposed more than 40 years ago (Burnet, F. M., 1967, Lancet 1(7501):1171-4), was supported in humans by epidemiological studies revealing a correlation between clinical immunosuppression and cancer development (Keast, D., 1970, Lancet 2(7675):710-2). Tumor immunosurveillance was only recently demonstrated through the use of tumor-prone immuno-deficient mice (Smyth et al. 2001, Nat. Immunol. 2(4)293-9; Shankaran et al., 2001, Nature 410(6832):1107-11). Since then, the capacity of both the innate and the adaptive immune systems to affect the course of tumor development has been shown in several mouse models (Pardoll, D. M., 2001, Science 294 (5542):534-6; Lanier, L. L., 2001, Nat. Med. 7(11):1178-80), and more recently in patients receiving a tumor-specific vaccine (Banchereau et al., 2001, Cell 106(3):271-4). However, the role of T-cell mediated immune response of clinically uncompromised patients in controlling the course of their tumors remains poorly documented.

The discovery and clinical validation of markers for cancer of all types which can predict prognosis and likelihood of invasive or metastatic spread is one of the major challenges facing oncology today. In breast cancer, 70% of the 186,000 annual cases present as lymph node negative; however, 30% of these cases will recur after local therapy (mastectomy or lumpectomy) (Boring et al., 1992, Clin. J. Cancer 42:19-38). Although adjuvant chemotherapy has been demonstrated to improve survival in node negative breast cancer patients (Mansour et al., 1989, Engl. J. Med. 485-490), it remains uncertain how to best identify patients whose risk of disease recurrence exceeds their risk of significant therapeutic toxicity (Osbourne, 1992, J. Clin. Oncol. 10:679-82).

In primary breast cancer, dendritic cells (DC) have been shown to infiltrate breast tumors (Bell et al., 1999, J. Exp Med. 190(10):1417-26) and antibodies directed against p53 (Lenner, et al., 1999, Br. J. Cancer 79(5-6):927-32) or HER2/neu (Disis et al., 1997, Adv. Cancer Res. 71:343-71) have been detected in patient serum. However, an efficient anti-tumor immune response has never been demonstrated. Indeed, in contrast with other tumor types, the incidence of breast cancer is rather reduced in immunocompromized patients (Stewart et al., 1995, Lancet 346(8978):796-8), and there has been one report to suggest that non-specific immunostimulating therapies may worsen the prognosis (Stewart et al., 1993, Clin. Exp. Metastasis 11(4):295-305). More recently, it has been shown that primary breast carcinoma are infiltrated with immature DC, leaving mature DC at the periphery of the tumor (Bell, et al., 1999, J. Exp. Med. 190(10):417-26; Suzuki, et al., 2002, J. Pathol. 196(1):37-43). However, the clinical relevance of this observation remains unclear, since immature DC infiltration in primary breast carcinoma does not seem to correlate with improved survival (Lewko et al., 2000, Med. Sci. Monit. 6(5):892-5; Lespagnard et al.,1999, Int. J. Cancer, 84(3):309-14) in contrast with other tumor types (Furukawa et al., 1985, Cancer, 56(11):2651-6; (Ambe et al., 1989, Cancer, 63(3): 496-503; Gallo et al., 1991, Arch. Otolaryngol Head Neck Surg. 117(9):1007-10; Goldman et al.,1998, Arch. Otolaryngol Head Neck Surg. 124(6):641-6).

Plasmacytoid DC (pDC) are a DC subset characterized by their ultrastructural resemblance to Ig-secreting plasma cells upon isolation from tonsils (Grouard et al., 1997, J. Exp. Med. 185(6): 1101-1111), their unique surface phenotype (CD4+IL-3R++CD45RA+HLA-DR+) (Grouard et al., 1997, J. Exp. Med. 185(6):1101-1111; Facchetti et al., 1999, Histopathology 35(1):88-9; Res et al., 1999, Blood 94 (8):2647-57), and their ability to produce high levels of type I IFN and induce potent in vitro priming with either Th1, Th2 or even Ts polarization, depending on the activation conditions (Cella et al., 2000, Nat Immunol 1(4):305-10; Kadowaki et al., 2000, J Exp Med 192 (2):219-26). pDC are believed to be derived from a precursor common with T cells and B cells (Grouard et al., 1997, J. Exp. Med. 185, 6:1101-1111; Res et al., 1999, Blood 94, 8:2647-57; Bruno et al., 1997, J. Exp. Med. 185:875-884; Bendriss-Vermare et al., 2001, J.Cl. 107:835; Spits et al., 2000, J. Exp. Med. 192 (12):1775-84).

In addition to their morphology, their type I IFN production and their putative origin, pDC also differ from myeloid DC in their weak phagocytic activity (Grouard et al., 1997, J. Exp. Med. 185(6):1101-1111), their weak IL-12 production capacity (Rissoan et al., 1999, Science 283:1183-1186), and the signals inducing their activation (Kadowaki et al., 2001, J. Immunol 166(4):2291-5). While recruitment of activated pDC should initiate immunity through naive T cell activation, immature DC have been reported to induce immune tolerance, likely through induction of regulatory T cells (Jonuleit et al., 2001, Trends Immunol. 22:394; Bell et al., 2001, Trends Immunol. 22:11; Roncarolo et al., 2001, JEM 193:F5; Jonuleit et al., 2000, JEM 162:1213). Moreover, pDC have been shown to induce IL-10 secreting T cells (Rissoan et al., 1999, Science 283:1183; Liu et al., 2001, Nature Immunol. 2:585) and CD8 regulatory T cells (Gilliet et al.,2002, J. Exp. Med. 195(6):695-704). In addition, active recruitment of pDC in ovarian tumors has been reported (Curiel et al., 2001, Keystone Symposia Mar. 12-18, 2001: Dendritic Cells, Interfaces With Immunobiology and Medicine; Zou, et al., 2001, *Nat Med,* 7(12):1339-46), suggesting that pDC may be favorable to tumor development in certain circumstances, likely through induction of regulatory immune responses. In these cases, the tumor environment is suspected to prevent activation of pDC. Furthermore, increased number of pDC has been recently associated with auto-immune diseases, in particular with Lupus (Farkas et al., 2001, *Am. J. Pathol.* 159:237).

In regard to the continuing need for materials and methods useful in making clinical decisions on adjuvant therapy, markers of tumor immunosurveillance are attractive candidates whose prognosis value have to be statistically demonstrated.

SUMMARY OF THE INVENTION

The present invention fulfills the foregoing need by providing methods for predicting the prognosis of disease course in cancer. It has now been discovered that there is a strong correlation between pDC infiltration of primary invasive, non-metastatic breast carcinomas and poor survival rates. This discovery provides a new tool to guide the diagnosis and treatment of breast cancer patients.

Thus, the invention provides a method for making a prognosis of disease course in a human cancer patient comprising the steps of (a) obtaining a sample of a tumor from the human cancer patient; and (b) detecting infiltration by plasmacytoid dendritic cells (pDC); wherein infiltration by plasmacytoid dendritic cells is prognostic of the agressiveness and mortality of the cancer.

In preferred embodiments, the cancer is primary breast cancer.

DETAILED DESCRIPTION OF THE INVENTION

All references cited herein are incorporated in their entirety by reference.

The present invention is based in part on the discovery that primary breast carcinomas are frequently infiltrated by immature and/or mature MDC, but only rarely by pDC. Surprisingly, pDC infiltration has been discovered to be a major prognostic factor for outcome in primary invasive non-metastatic breast cancer.

The nature of the T cell response upon presentation of antigen by DC is dependent on the subpopulation of DC involved and the stage of maturation of presenting DC (Steinman et al., 2000, *J. Exp. Med.* 191(3): 411-6). Despite functional plasticity, MDC and pDC tend to polarize the type of the T cell response toward a Th1 or a Th2 response through their capacity to secrete IL-12 or not, respectively (Rissoan et al., 1999, *Science* 283(5405):1183-6). The two DC subtypes also make different links between acquired and innate immune responses, with MDC activating both B cells (Dubois et al., 1999, *J. Leukoc. Biol.,* 66(2):224-30) and NK cells (Zitvogel et al., 2002, *J. Exp. Med.* 195(3):F9-14), and pDC producing large amounts of natural IFNs in response to viruses (Liu, Y. J., 2001, *Cell* 106(3):259-62).

In view of the various reported functional differences between pDC and MDC, the inventors have investigated the role of DC in the biology of early breast cancer. The inventors studied tumor tissue from a total of 255 patients with primary invasive non metastatic breast carcinomas. These studies led to the discovery that there is a striking unfavorable prognostic value for overall survival (OS) and relapse-free survival (RFS) of the presence of CD123$^+$ pDC in the tumor in both univariate and multivariate analyses. While the presence of pDC in breast metastatic lymph node (Horny, et al., 1987, *Hum. Pathol.* 18(1):28-32) or in malignant ascites (Zou et al. 2001 Nat. Med. 7(12):1339-46) had been previously reported, the present invention represents the first attempt to correlate pDC tumor infiltrate with clinical data. In the 1996 series, patients with pDC infiltrates in the primary tumor had only a 37% relapse-free and a 50% overall survival at 5 years. In marked contrast with the poor outcome of tumors containing CD123$^+$ pDC, patients with tumors not infiltrated by CD123$^+$ pDC had a favorable evolution: regardless the size of the primary tumors or the lymph node status, subgroups of patients with T1-2, T3-4, and N+ tumors without CD123$^+$ infiltrating pDC all had and overall survival over 90% at 5 years.

The description of a strong correlation between pDC infiltration in breast tumor and poor prognosis provides a novel prognostic marker for primary breast cancer that could assist in deciding how to optimize the use of the current treatments, and provide a useful tool for the design and the interpretation of therapeutic protocols.

The methods of the invention thus provide a means for making a prognosis of disease course in a human patient having cancer comprising detecting pDC infiltration in breast tumors. pDC infiltration can be detected directly by obtaining a sample of a tumor from a human cancer patient and testing for specific pDC markers such as CD123, using antibodies specific for said markers. For example, the anti-CD123 monoclonal antibody used in the studies described herein, mouse mAb SS DCYL 107D2, was cloned after immunizing mice with human enriched pDC (Schering Plough). Other antibodies suitable for use in the methods of the invention are described in U.S. Pat. No. 5,541,063. Alternatively, pDC infiltration might be determined by: 1) detection of other pDC-specific markers on tissue section such as BDCA2; 2) detection of pDC-secreted type I IFN on tissue section; 3) detection of type I IFN-induced markers on tissue section, such as MXA; 4) detection of pDC or of pDC-related products in other sites, i.e. type I IFN in circulating blood.

EXAMPLES

The invention can be illustrated by way of the following non-limiting examples, which can be more easily understood by reference to the following materials and methods.

Patient Selection

Two series of patients were studied: these are referred to herein as "the 1996 series" and "the 1997 series".

A. The 1996 Series

All clinical and biological data on early breast cancer were collected prospectively and included in a regularly updated computer database at Centre Leon Berard (CLB) since 1996. The first 152 patients with early breast cancer treated in the CLB since Sep. 1, 1996 were analyzed. They all received treatment according to the same standard protocol. Patients characteristics are presented in Table 1. The median follow up of the series is 60 months (range 2-72).

B. The 1997 Series 103 patients with early breast cancer treated in the CLB since Jun. 1, 1997 were analyzed in a validation study. They all received treatment according to the same standard protocol. Patients characteristics are as follows: TO: 9, T1:56; T2:29, T3:2; T4:1, respectively; information was not available for 7 tumors. "Node negative n=61, 59%, N+1-3: n=29, 28%, N4-8, n=6, 6%, N>8, n=8, 8% respectively. SBR 1,2,3 in 20, 51 and 29% of samples respectively. ER+ or PgR+ in 92 (91%). The median follow up of the series is 58 months (range 6-68 months)."

Treatment

Patients from both the 1996 series and the 1997 series were treated according to the following procedures: mastectomy for central tumors or tumors larger than 3 cm, conservative surgery followed by radiotherapy for the remaining patients. Adjuvant chemotherapy with anthracyclins was given to node positive patients and to node negative patients with two or more of the following criteria: tumor larger than 3 cm, SBR grade 2-3, negative ER and PgR expression. Neoadjuvant chemotherapy with anthracyclins was given to T4d tumors. Tamoxifen 20 mg/day was given during 5 years in patients with ER or PgR expressing tumors.

Immunohistochemistry

Paraffin embedded breast tumors were used for the analyses. Slides were reviewed and the blocks containing invasive carcinoma were serially sectioned at a thickness of 4 µm. After deparaffinization and rehydratation, endogenous peroxidases were blocked by incubating the slides in 5% hydrogen peroxide in sterile water. For heat induced antigen retrieval, tissue sections were boiled in 10 mM citrate buffer pH6 using either a microwave for 15 minutes [anti-CD3 rabbit polyclonal (Dako, Trappes, France); anti-CD1a mouse clone 010 (Beckman-Coulter, Marseille, France); anti-DC-LAMP rat clone 1010E1 (Schering-Plough, Dardilly, France); anti-Langerin mouse clone 310F7 (Schering-Plough, Dardilly, France); anti-CCR6 mouse clone 53103-111 and anti-CCL19 goat polyclonal (R&D Systems, Minneapolis, USA)] or a water bath for 40 minutes [anti-hCCL21 polyclonal (R&D Systems, Minneapolis, USA)]. No antigen retrieval was performed for the following antibodies: anti-CCR7 mouse clone 2H4 (Pharmingen, San Diego, USA), anti-CD123 mouse clone 107D2 (Schering-Plough, Dardilly, France) and anti-CD68 mouse clone PGM1 (Beckman-Coulter, Marseille, France). Non specific binding was blocked with a protein blocking reagent (Beckman-Coulter, Marseille, France) for 5 minutes except for antibodies anti-CD123 (10 minutes), anti-CD1a and anti-CCL19 (15 minutes). The slides were then incubated at room temperature for one hour with the primary antibodies from the list above. These antibodies were used directly (anti-CD1a and anti-CD68-PGM1) or were diluted using an antibody diluent (Dako, Trappes, France) at respectively 1/25 (anti-CCL19), 1/50 (anti-hCCL21), 50 µg/ml (anti-Langerin), 1/200 (anti-CD3), 0.5 µg/ml (anti-DC-LAMP), 5 µg/ml (anti-CD123), 1/500 (anti-CCR7) and 1/1500 (anti-CCR6). For the negative control slides, the primary antibody was replaced by a non immune serum. After rinsing in Phosphate Buffered Saline, the slides were incubated with a biotinylated secondary antibody bound to a streptavidin peroxidase conjugate [Ultratech HRP DAB kit (Beckman-Coulter, Marseille, France) or LSAB+ kit (Dako, Trappes, France) for anti-CCL19 and anti-hCCL21. Bound antibody was revealed by adding the substrate 3,3'-diamino benzidine. Sections were counterstained with hematoxylin. After dehydratation and mounting, they were analyzed independently by both the pathologist and the technician. Upon the observation of the first 30 cases, a grading system was defined in which the density of positive cells within the tumor was assessed semi-quantitatively for each antibody. This classification allowed the stratification of the tumors for each staining in either 2 groups (CD123 positive cells) or 3 groups (CD68, CCR7, CD3, positive cells; CD1a, CD207/ Langerin, CD208/DC-LAMP, CCL19 and CCL21 positive DC). A slide which was representative for each group was then used as control for the analysis of the subsequent 120 cases. For antibodies against CCR6, CCL19 and CCL21, both the intensity of the staining (3 grades) and the percentage of positive tumor cells, and the frequency of positive infiltrating cells was assessed semi-quantitatively.

For BDCA2/CD123 double staining, immunohistochemistry was performed on specimens obtained from the corresponding breast tumors stored in liquid nitrogen. Eight µm frozen sections were cut and fixed with cold acetone for 20 min at 4° C. Endogenous peroxidases were blocked with $H_2O_2$ (0.3% in PBS), Endogenous biotin was blocked with an appropriate kit (Vector Laboratories, Inc, Burlingame, Calif.) and sections were saturated with goat serum (2% in PBS for 30 min). Sections were then incubated at room temperature for one hour with the primary antibodies: 20 µg/ml anti-BDCA2 (Miltenyi Biotec, GmbH) or mouse IgG1 (Dako). The slides were then incubated for 30 min. with a biotinylated goat anti-mouse IgG1 mAb (Caltag Laboratories, Inc., Burlingame, Calif.) followed by incubation with extravidin peroxidase (Sigma, Aldrich, St. Louis, Mich.). Peroxidase activity was revealed using 3 amino-9-ethyl-carbazole (Vector Laboratories). Slides were then saturated with mouse serum (2% in PBS for 30 min) and incubated with anti-CD123 IgG1 mAb (clone 9F5, Pharmingen, San Diego, Calif.) or IgG1biot (Dako) for one hour. Sections were incubated with streptavidin-alkaline phosphatase conjugate. This activity was revealed with Alkaline phosphatase substrate kit III (Vector Laboratories).

Statistical Analysis

The correlation between the clinico-biological data and the phenotype of both tumor and stromal cells within the tumor was performed using the chi2 test or Fisher exact test. The correlation between the different phenotypic markers of immune cells was also tested using the Pearson test. Survival curves were plotted using the Kaplan Meier method, and survival was compared using the logrank test. Multivariate analysis of prognostic factors for overall and relapse free survival were performed using the Cox model. All statistical analysis were done using the procedures of the SPSS 10.02 package.

Example 1

Immune Cell Infiltration, Chemokine and Chemokine Receptor Expression in Breast Tumors Several parameters were selected for investigation: CD1a and Langerin, two markers of Langerhans-type immature DC; CD123, a marker of pDC; and DC-LAMP, a molecule expressed specifically by mature DC (de Saint-Vis et al., 1998, *Immunity*, 9(3):325-36) were analyzed. Immunostaining was also performed for analyzing the expression of chemokine receptors CCR6 and CCR7, and of their ligands MIP3α and CCL19 (MIP-3β) or hCCL21 (6Ckine), which are known to drive immature and mature DC migration, respectively (Dieu et al., 1998, J. Exp. Med. 188(2):373-86). In addition, CD3+ lymphocytes and CD68+ macrophages infiltrates were studied.

Table 1 describes the presence and phenotype of immune cells, as well as the chemokine and chemokine receptor expression pattern in the 1996 series of 152 patients with non metastatic breast cancer tumors. 112 tumors from this series were infiltrated by dendritic cells.

TABLE 1

Description of the "1996 series" patients

|  | N(%) |
|---|---|
| Age | 56 (30-89) |
| Tumor size (T) | |
| 0 | 17 (11) |
| 1 | 44 (29) |
| 2 | 45 (30) |
| 3 | 15 (10) |
| 4 | 31 (20) |
| Number of involved lymph nodes | |
| 0 | 61 (40) |
| 1-3 | 52 (35) |
| 4-8 | 18 (12) |
| >8 | 21 (13) |
| SBR | |
| 1 | 40 (26) |
| 2 | 67 (44) |
| 3 | 45 (30) |
| ER | |
| 0 | 37 (24) |
| + | 115 (76) |
| PgR | |
| 0 | 43 (28) |
| + | 109 (72) |
| ER & PgR | |
| 0 | 23 (15) |

Immune markers:

| | Proportion of positive cells | | | | |
|---|---|---|---|---|---|
| | 0 | + | ++ | +++ | Total+ |
| Cells in the stroma | | | | | |
| CD3 | 27 (17) | 63 (41) | 38 (25) | 24 (16) | 125 (82) |
| CD68 | 30 (20) | 91 (60) | 25 (17) | 5 (3) | 121 (70)* |
| DC Lamp | 67 (44) | 55 (36) | 26 (17) | 3 (2) | 84 (56)* |
| Langerin | 106 (70) | 33 (22) | 9 (6) | 4 (3) | 46 (30) |
| CD1a | 111 (73) | 23 (15) | 13 (9) | 5 (3) | 41 (27) |
| CD123 | 132 (87) | 18 (12) | 2 (1) | 0 | 20 (13) |
| On tumor cells and cells in the stroma | | | | | |
| MIP3β | 66 (43) | 32 (21) | 42 (28) | 11 (7) | 85 (57)* |
| 6CK | 141 (93) | 8 (5) | 3 (2) | 0 | 11 (7) |

*one missing observation
*CD68, CCR6, DC Lamp, MIP3β expression was not interpretable in one sample.

As can be seen in Table 1, 56% of the tumors contained DC-LAMP+ mature dendritic cells (Stewart, 1995, *Lancet* 346(8978):796-8), which were consistently located within CD3+ T cell infiltrates. Indeed, a strong correlation between DC-LAMP expression and CD3+ T lymphocytes infiltrates was observed (r=0.73, p<0.0001). The striking compartimentalization of immature TIDC within tumor bed and mature TIDC within peritumoral clusters of T cells was confirmed (Bell et al., 1999, *J. Exp. Med.* 190(10):1417-26; Suzuki et al, 2002, *J. Pathol.* 196(1):37-43). A strong association between the presence of DC-LAMP+ and CD3+ cells was observed, but the density of both mature DC and T cell infiltrate did not correlate to the prognosis. Although the exact nature of DC-LAMP+ TIDC remains to be determined, the absence of overlapping localization with CD123+/BDCA-2+ cells on serial tissue sections suggests a non-plasmacytoid origin.

13% of the tumors had CD123+ cells exhibiting the typical morphology of pDC (Grouard, et al., 1997, *J. Exp. Med.* 185(6):1101-11). Using double staining (CD123, BDCA2) on frozen sections proceeding from the same tumors, these cells also expressed BDCA2, a specific marker for pDC (Dzionek, et al., 2001, *J. Exp. Med.* 194(12):1823-34). Of note, pDC CD123+ were never found within CD3+ T infiltrates, but would sometimes lay in the vicinity of tumor cells.

Langerhans-type DC were detected in about one third of primary breast tumors. This is in contrast with our previous report, where 32/32 frozen tissue sections were infiltrated by CD1a+ and/or Langerin+ DC (Bell et al., 1999, J Exp Med, 190(10):1417-26). Such difference might be due to sampling bias or may reflect a lower sensitivity of immunostaining on paraffin-embedded tissue section. Langerin+ DC and CD1a expressing DC had a specific spatial pattern merging into carcinomatous sheets.

H6CK/CCL21 and MIP3β/CCL19, two ligands for CCR7, were expressed (either by tumors cells, stromal cells or both) in 7% and 57% of the samples, respectively. Although the expression of these two chemokines did not correlate to tumor size, nodal status, SBR grade and hormone receptor status, CCL19 expression was associated in both univariate and multivariate analyses with a favorable OS (98% rate at five years) but not with RFS. The mechanisms underlying this observations is unclear: CCL19 may attract mature DC and T lymphocytes that both could contribute to control tumor progression (Vicari et al., 2000, *J. Immunol.* 165(4):1992-2000; Sharma et al., 2000, *J Immunol* 164(9):4558-63; Sharma et al., 2001, *Cancer Res,* 61(17):6406-12; Kirk et al., 2001, *Cancer Res,* 61(5):2062-70), but no correlation was observed between TIDC or CD3+ T cell infiltrates and either CCL19 expression or prognosis. MIP3α CCL20 was not detectable in the 1996 series. MIP3β/CCL19 and 6Ckine/CCL21 expression was observed both in tumor and DCs (Table 1). Of note, 6Ckine/CCL21 expression was also observed occasionally in lymphatic endothelial cells.

Example 2

Infiltration of Immune Cells and Clinico-biological Presentation of the Tumor

CD1a, CD68, Langerin, hCCL21, CCL19 expression did not significantly (p>0.01) correlate to the clinical and/or histological parameters of the primary tumors. The presence of DC-LAMP+ cells and CD3 infiltrating T cells, significantly correlated to the size of the tumor, the axillary lymph node involvement, a high SBR histological grade, and the lack of hormone receptor expression. Conversely, detection of CD123+ tumor infiltrating pDC (TIpDC) did not correlate with tumor size, nodal stage, SBR grade or hormone receptor status (Table 2).

TABLE 2

Correlations between tumor characteristics and DC or T cell infiltration

| | N (%) | CCR7 (%) on stromal cells | | | | | CD123 (%) on pDC | | | CD3 (%) in the stroma | | | | | DC Lamp (%) in the stroma | | | | CCR6 (%) on tumor cells | | | |
|---|---|---|---|---|---|---|---|---|---|---|---|---|---|---|---|---|---|---|---|---|---|---|
| | | 0 | + | ++ | +++ | | 0 | +/++ | | 0 | + | ++ | +++ | | 0 | + | ++/+++ | | 0 | + | ++ | |
| Age | | | | | | | | | | | | | | | | | | | | | | |
| <35 | 5 (3) | 20 | 40 | 0 | 40 | | 100 | 0 | | 0 | 0 | 60 | 40 | | 60 | 40 | 0 | | 20 | 40 | 40 | |
| 35-50 | 41 (27) | 37 | 34 | 27 | 2 | | 85 | 15 | | 22 | 34 | 22 | 22 | | 75 | 12 | 12 | | 68 | 22 | 9 | |
| >50 | 106 (70) | 24 | 32 | 31 | 12 | 0.04 | 87 | 13 | 0.03 | 17 | 45 | 24 | 13 | 0.33 | 68 | 24 | 8 | 0.55 | 53 | 29 | 17 | 0.36 |
| T | | | | | | | | | | | | | | | | | | | | | | |
| 0 | 17 (11) | 41 | 47 | 6 | 6 | | 94 | 6 | | 35 | 41 | 6 | 18 | | 82 | 18 | 0 | | 82 | 0 | 18 | |
| 1 | 44 (29) | 29 | 29 | 36 | 4 | | 91 | 9 | | 18 | 45 | 18 | 18 | | 52 | 30 | 18 | | 59 | 32 | 9 | |
| 2 | 45 (30) | 27 | 36 | 24 | 13 | | 87 | 13 | | 11 | 42 | 24 | 22 | | 73 | 18 | 9 | | 66 | 27 | 7 | |
| 3 | 15 (10) | 20 | 40 | 20 | 20 | | 93 | 7 | | 26 | 33 | 40 | 0 | | 93 | 0 | 7 | | 40 | 33 | 27 | |
| 4 | 31 (20) | 6 | 19 | 51 | 22 | 0.01 | 74 | 26 | 0.25 | 13 | 39 | 39 | 10 | 0.14 | 71 | 29 | 0 | 0.06 | 32 | 36 | 32 | 0.002 |
| N | | | | | | | | | | | | | | | | | | | | | | |
| 0 | 61 (40) | 29 | 39 | 25 | 7 | | 89 | 11 | | 21 | 54 | 16 | 8 | | 59 | 31 | 10 | | 66 | 28 | 7 | |
| >0 | 91 (60) | 21 | 27 | 35 | 16 | 0.07 | 86 | 14 | 0.61 | 15 | 33 | 31 | 21 | 0.004 | 34 | 40 | 26 | 0.005 | 50 | 28 | 22 | 0.06 |
| SBR | | | | | | | | | | | | | | | | | | | | | | |
| 1 | 40 (26) | 35 | 35 | 22 | 7 | | 97 | 3 | | 30 | 42 | 20 | 7 | | 59 | 26 | 15 | | 72 | 20 | 8 | |
| 2 | 67 (44) | 24 | 33 | 33 | 10 | | 82 | 18 | | 15 | 51 | 24 | 10 | | 48 | 37 | 15 | | 51 | 33 | 16 | |
| 3 | 45 (30) | 16 | 29 | 36 | 20 | 0.24 | 84 | 16 | 0.06 | 11 | 27 | 31 | 31 | 0.004 | 27 | 44 | 29 | 0.03 | 51 | 27 | 22 | 0.22 |
| Hormone receptors | | | | | | | | | | | | | | | | | | | | | | |
| 0 | 23 (15) | 22 | 26 | 44 | 9 | | 83 | 17 | | 9 | 17 | 26 | 48 | | 22 | 26 | 52 | | 70 | 22 | 9 | |
| + | 129 (85) | 25 | 33 | 29 | 13 | 0.55 | 88 | 12 | 0.51 | 19 | 46 | 25 | 10 | 0.000 | 48 | 38 | 13 | 0.000 | 54 | 29 | 17 | 0.54 |

Example 3

Survival and Immune Cell Infiltration

As expected, overall survival (OS) and relapse free survival (RFS) were significantly reduced in patients with large tumors, nodal involvement and high SBR grade (Table 3). In addition, in univariate analysis, the presence CD123+ cells was identified as an adverse prognostic factor for both overall and relapse free survival, while the presence of MIP3β/CCL19 was significantly associated with an improved overall but not relapse free survival (Table 3). CD1a, Langerin, CD3, DC-LAMP, hCCL21 and CD68 expression did not correlate to either OS or RFS.

TABLE 3

Prognostic parameters for survival in univariate analysis

| | N (%) | Relapse free survival | | Overall survival | |
|---|---|---|---|---|---|
| | | 5 year survival (%) | logrank | 5 year survival (%) | logrank |
| Age | | | | | |
| <35 | 5 (3) | 80 | | 100 | |
| 35-50 | 41 (27) | 80 | | 90 | |
| >50 | 106 (70) | 90 | 0.42 | 87 | 0.56 |
| T | | | | | |
| 0 | 17 (11) | 94 | | 100 | |
| 1 | 44 (29) | 95 | | 92 | |
| 2 | 45 (30) | 88 | | 88 | |
| 3 | 15 (10) | 70 | | 90 | |
| 4 | 31 (20) | 65 | 0.01 | 73 | 0.04 |
| Ax. node involved | | | | | |
| 0 | 61 (40) | 92 | | 93 | |
| 1-8 | 70 (47) | 87 | | 89 | |
| >8 | 21 (13) | 54 | 0.0001 | 74 | 0.007 |
| SBR | | | | | |
| 1 | 40 (26) | 100 | | 100 | |
| 2 | 67 (44) | 78 | | 85 | |
| 3 | 45 (30) | 86 | 0.01 | 81 | 0.02 |
| HR | | | | | |
| 0 | 23 (15) | 85 | | 80 | |
| + | 129 (85) | 86 | 0.83 | 90 | 0.07 |
| DC Lamp* | | | | | |
| 0/+ | 122 (80) | 86 | | 90 | |
| ++/+++ | 29 (19) | 93 | 0.43 | 86 | 0.54 |
| CD123 | | | | | |
| 0 | 132 (87) | 90 | | 93 | |
| +/++ | 20 (13) | 37 | 0.0000 | 58 | 0.0001 |

TABLE 3-continued

Prognostic parameters for survival in univariate analysis

|  | N (%) | Relapse free survival | | Overall survival | |
|---|---|---|---|---|---|
|  |  | 5 year survival (%) | logrank | 5 year survival (%) | logrank |
| MIP3β |  |  |  |  |  |
| 0/+ | 98 (64) | 83 |  | 85 |  |
| ++/+++ | 54 (36) | 85 | 0.68 | 95 | 0.02 |

*in one tumor, DC Lamp expression was not interpretable

Multivariate analysis showed that node involvement and CD123+ pDC infiltration were independent prognosis factors for RFS and OS. SBR grading was an independent prognostic factor for RFS, while the presence of CCL19 was an independent prognostic factor for OS only (Table 4).

TABLE 4

Multivariate analysis of prognostic factors for survival

|  | Beta | SE | p | risk |
|---|---|---|---|---|
| Relative Relapse free survival |  |  |  |  |
| Presence of CD123+ cells | 2.53 | 0.44 | 0.000 | 12.6 |
| Number of involved nodes | 0.12 | 0.02 | 0.000 | 1.13 |
| SBR | 0.59 | 0.32 | .06 | 1.73 |
| Overall survival (with MIP3b) |  |  |  |  |
| Presence of CD123+ cells | 2.66 | 0.58 | 0.000 | 14.3 |
| Number of involved nodes | 0.119 | 0.03 | 0.000 | 1.13 |
| Presence of MIP3β+ cells | −2.14 | 0.78 | 0.006 | 0.12 |
| Overall survival (without MIP3b) |  |  |  |  |
| Presence of CD123+ cells | 1.879 | .523 | .000 | 6.544 |
| Number of involved nodes | .108 | .031 | .001 | 1.114 |
| SBR | .957 | .401 | .017 | 2.603 |

Example 4

The 1997 Validation Series

To confirm the prognostic value of the presence of CD123+ DC in primary breast carcinoma, the inventors tested the prognostic value of this parameter in the validation series of the 103 first patients included in the prospective database in 1997. 11 (11%) of the tumors contained pDC in this validation series, as compared to 13% in the test series described above. Overall survival at 60 months was 92% in the pDC negative subgroup vs 70% in the pDC+ subgroup (p=0.05). Relapse free survival at 60 months was 89% in the pDC negative subgroup vs 36% in the pDC+ subgroup (p=0.03).

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for making a prognosis of disease course in a human patient having cancer comprising detecting infiltration of a tumor by plasmacytoid dendritic cells (pDC), wherein infiltration by plasmacytoid dendritic cells is prognostic of the aggressiveness and mortality of the cancer, and wherein said detecting of infiltration of a tumor by pDC comprises testing for secondary pDC markers in the circulating blood, wherein said secondary pDC markers are selected from the group consisting of type 1 IFN and MXA.

2. The method of claim 1, wherein the cancer is primary breast cancer.

3. The method of claim 2, wherein the cancer is primary invasive, non-metastatic breast cancer.

4. The method of claim 1, wherein said secondary pDC marker is type 1 IFN and MXA.

5. The method of claim 1, wherein said secondary pDC marker is MXA.

* * * * *